United States Patent [19]

Montoya et al.

[11] 4,240,290

[45] Dec. 23, 1980

[54] SKIN FRICTION MEASURING DEVICE FOR AIRCRAFT

[75] Inventors: Lawrence C. Montoya; Donald R. Bellman, both of Lancaster, Calif.

[73] Assignee: The United States of America as represented by the Administrator of the National Aeronautics and Space Administration, Washington, D.C.

[21] Appl. No.: 64,617

[22] Filed: Aug. 7, 1979

[51] Int. Cl.³ ............................................. G01C 21/00
[52] U.S. Cl. ...................................... 73/178 R; 73/147
[58] Field of Search ......................... 73/147, 9, 178 R

[56] References Cited

U.S. PATENT DOCUMENTS

| 2,935,870 | 5/1960 | Lyons, Jr. | 73/147 |
|---|---|---|---|
| 3,304,775 | 2/1967 | Kistler | 73/147 |
| 3,383,914 | 5/1968 | MacArthur | 73/147 |
| 3,460,383 | 8/1969 | Padera | 73/147 |
| 3,714,824 | 2/1973 | Bush | 73/147 |
| 4,112,752 | 9/1978 | Hafner et al. | 73/147 |

FOREIGN PATENT DOCUMENTS 151494  10/1962  U.S.S.R. .................................. 73/147

*Primary Examiner*—Donald O. Woodiel
*Attorney, Agent, or Firm*—Monte Mott; John R. Manning; Paul F. McCaul

[57] ABSTRACT

A skin friction measuring device for measuring the resistance of an aerodynamic surface to an airstream, adapted to be mounted on an aircraft, within an opening defined therein, and characterized by a friction plate adapted to be disposed in a flush relationship with the external surface of the aircraft and be displaced in response to skin-friction drag, as an airstream is caused to flow over the surface thereof, and a potentiometer connected to the plate for providing an electrical output indicative of the magnitude of the drag.

5 Claims, 8 Drawing Figures

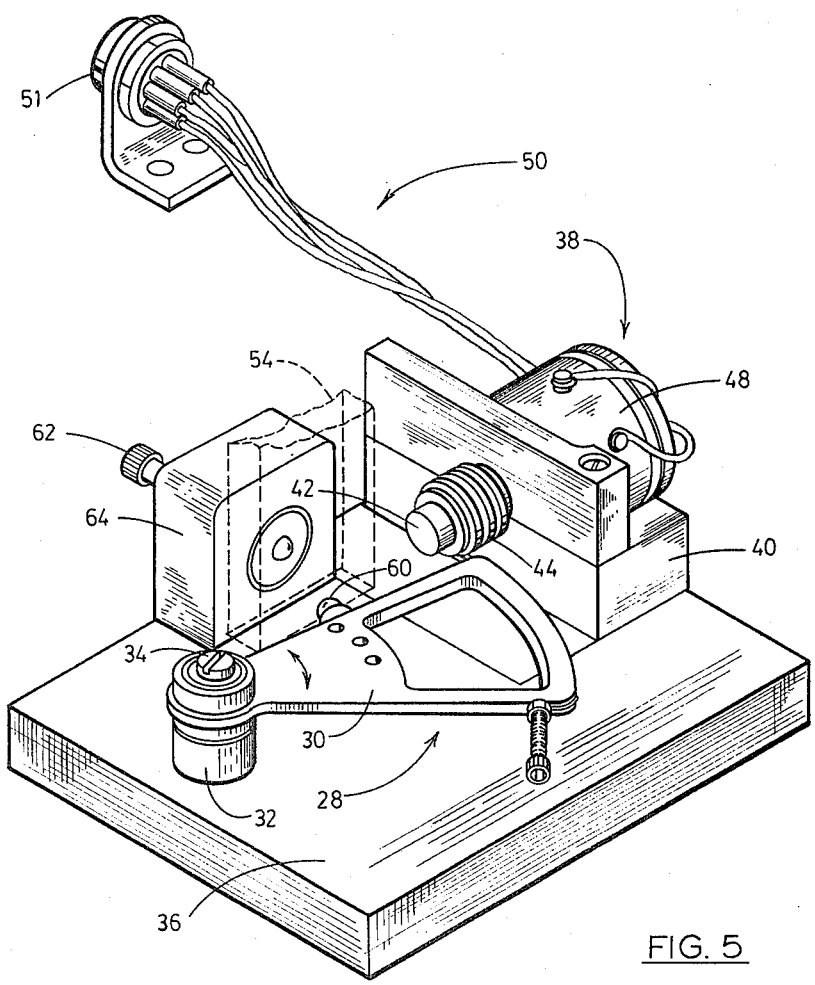
FIG. 5
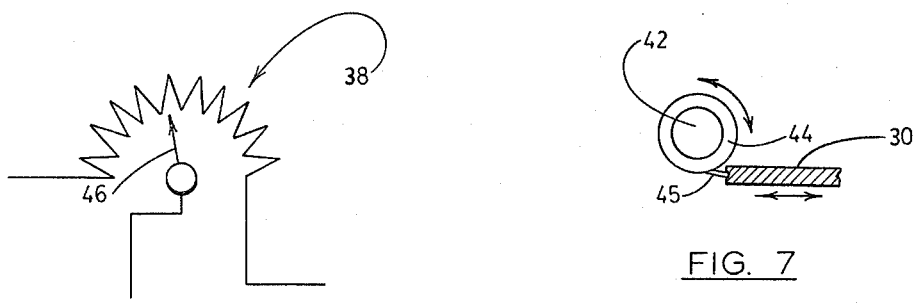
FIG. 8
FIG. 7

SKIN FRICTION MEASURING DEVICE FOR AIRCRAFT

ORIGIN OF THE INVENTION

The invention described herein was made in the performance of work by employees of the United States Government and may be manufactured and used by or for the Government for Governmental purposes without the payment of any royalties thereon or therefor.

BACKGROUND OF THE INVENTION

1. Field of the Invention:

As is well known, various surface characteristics tend to vary the resistance offered by the skin of an aircraft in flight to an airstream flowing thereover. For example, rivet heads, surface textures, finishes and the like, all tend to offer resistance to an airstream as it is caused to flow thereover. Such resistance, herein referred to as skin friction, creates drag, herein referred to as skin-friction drag, which significantly tends to impair the overall operational efficiency of an aircraft.

The instant invention generally relates to a device particulaly suited for use in studying shear force on aircraft in flight and more specifically to an improved skin friction measuring device which is of a large rugged construction, economic to fabricate, simple to operate and characterized by small displacement, preferably on the order of 0.005 to 0.010 inches. The skin friction measuring device which embodies the principles of the instant invention is particularly adapted to be mounted aboard subsonic aircraft and employed in obtaining research and design data, as it relates to the skin friction characteristics of the aircraft in flight, however, it is to be understood that the invention is equally useful in wind-tunnel environments.

2. Description of the Prior Art:

During the course of a preliminary search conducted for the invention, a patent to Hafner et al No. 4,112,752 was discovered. This patent discloses a force measuring device adapted to be moved between hydrostatic bearings and employs strain gauges for providing outputs indicative of the force components exerted by a flowing medium.

Additionally, U.S. Pat. No. 2,935,870 was discovered. This patent discloses a skin friction measuring device sensitive to acceleration forces and is adapted to support segments of the surface of a missile.

A patent to Kistler U.S. Pat. No. 3,304,775 also was discovered. This patent discloses an aerodynamic drive measuring device. In operation, movement through a medium of a vehicle in which the device is mounted produces a driving force on a sensing element which, in turn, is detected as a change in capacitance in a sensing circuit.

A patent to MacArthur U.S. Pat. No. 3,383,914 was discovered which discloses a skin friction transducer wherein a shear sensitive element is supported for a strap connected to a piezoelectric element. In operation, a flow is directed across the surface of the sensing element causing the piezoelectric element to deflect for producing a voltage, the magnitude of which is proportional to the deflection.

A patent to Padera U.S. Pat. No. 3,460,383 also was discovered. This patent discloses a control surface for aerodynamic or hydrodynamic models having flexured areas so configured as to enable accurate utilization of strain gauges or the like on the exterior of control surfaces.

Finally, a patent to Bush U.S. Pat. No. 3,714,524 was discovered. The patent to Bush discloses a skin friction measuring apparatus. However, the patented apparatus differs substantially in structure from the invention hereinafter more specifically described.

While, as should now be apparent, various devices have been proposed for use as skin friction measuring devices, it has in practice been found that the previously employed skin friction measuring devices simply fail to provide the data necessarily required for the design of operationally efficient aircraft. As a consequence of this inadequacy, tests have been delayed, inaccurate data obtained, and significant expense have been encountered in conducting routine experiments, to say nothing of the costs encountered in the repair and maintenance of the devices previously employed.

It is, therefore, the general purpose of the instant invention to provide a simple, rugged, practical and economically feasible skin friction measuring device which is particularly adapted to be employed in a test station environment for routinely studying the resistance offered to fluids caused to flow across the skin of an aircraft in flight, herein simply referred to as a skin friction measuring device.

OBJECTS AND SUMMARY OF THE INVENTION

It is therefore an object of the instant invention to provide a simple, practical and economic skin friction measuring device for aircraft.

It is another object to provide a skin friction measuring device which is of a rugged construction, simple to operate and economic to fabricate.

It is another object to provide a simple, accurate, economic and rugged skin friction measuring device having a capability of providing accurate intelligence indicative of skin friction as an airstream is caused to pass over the surface of an aircraft in flight.

These and other objects and advantages are achieved through a use of a base plate adapted to be mounted within an air frame, a friction plate adapted to be disposed in contiguous relation with an airstream, a plurality of flexural members mounting the friction plate on the base plate and supporting the friction plate for skin-friction drag induced displacement as an airstream is caused to pass over the aircraft, and motion measuring means connected to the friction plate and adapted to respond to the induced displacement thereof for providing an electrical signal comprising a measurement of drag, on the order of 0.02 pounds whereby the magnitude of the skin friction for given surfaces may be determined, as will become more readily apparent by reference to the following description and claims in light of the accompanying drawings.

DESCRIPTION OF THE DRAWINGS

FIG. 5 is a perspective view of the interconnected pivotal arm and potentiometer shown in FIG. 4.

FIG. 7 is a fragmented view depicting one manner in which the potentiometer is interconnected with the pivotal arm.

FIG. 8 is a schematic view of the potentiometer.

DESCRIPTION OF THE PREFERRED EMBODIMENT

Figure 1:
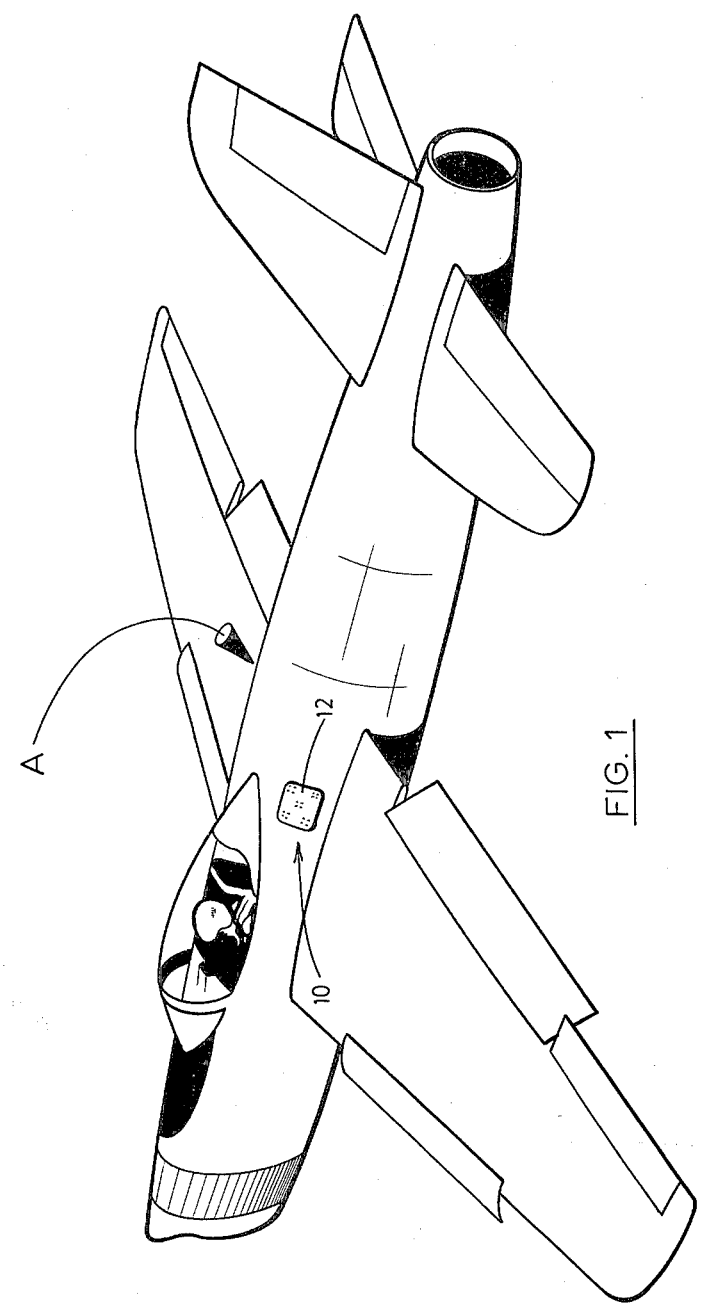
FIG. 1 is a perspective view of an aircraft depicting an environmental view for the skin friction measuring device which embodies the principles of the instant invention.

Referring now to the drawings wherein like reference characters designate like or corresponding parts throughout the several views, there is shown in FIG. 1 an aircraft A having a fuselage within which is mounted a skin friction measuring device, generally designated 10, which embodies the principles of the instant invention. It will be appreciated that the device 10 may be mounted at any suitable location, not limited to the fuselage as shown.

It is important to note that the device 10 includes a friction plate 12 having an external surface not designated but preferably conforming in its configuration to the configuration of the external surface of the fuselage and supported in a flush relationship therewith. Thus the skin friction measuring device 10 provides a substantially uninterrupted surface, as "seen" by an airstream as it is caused to flow over the fuselage when the aircraft is in flight.

Figure 2:
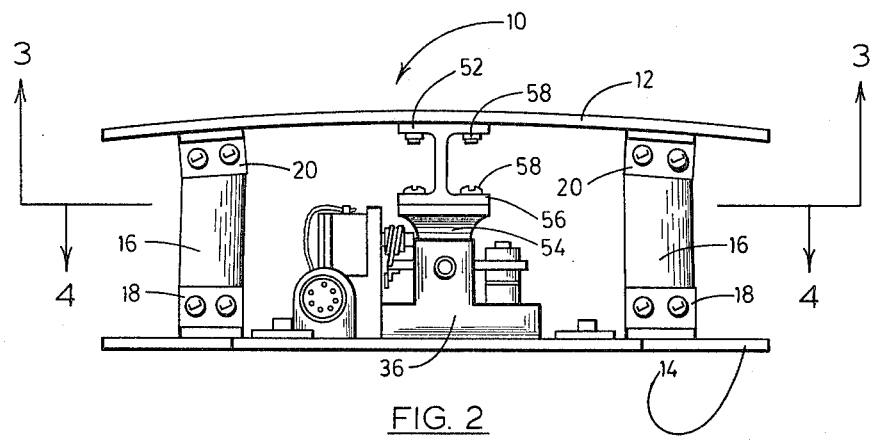
FIG. 2 is an end elevational view of the device.
Figure 3:
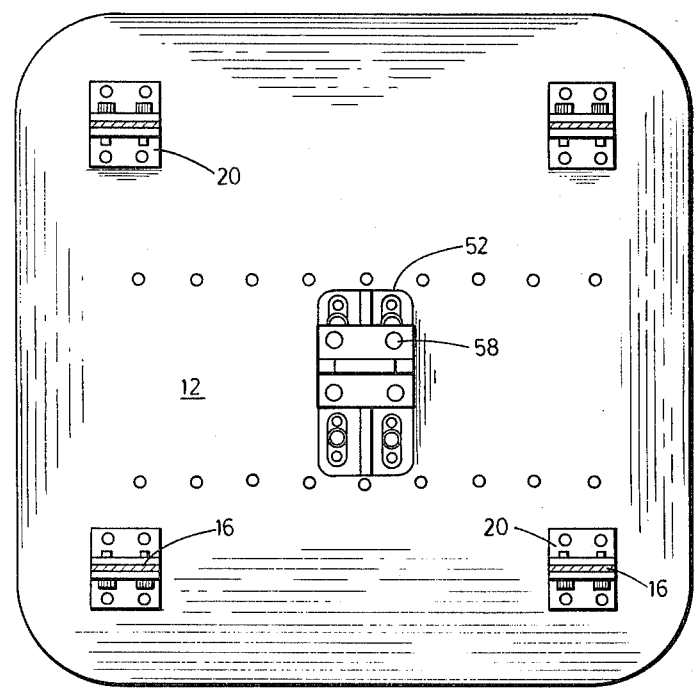
FIG. 3 is a sectioned view taken generally along lines 3—3 of FIG. 2.

As shown in FIG. 2, the friction plate 12 is mounted on a base plate 14 through the use of flexural members 16. Each of the flexural members 16 comprises a flat, resilient member characterized by a suitable spring constant which permits the members to deflect in response to skin-friction drag, or forces applied to the friction plate by an airstream as it is caused to flow thereover.

The flexural members 16 are attached to the base plate 14 through the use of brackets 18 and to the friction plate 12 through the use of brackets 20, similar in design and function to the brackets 18.

Figure 4:
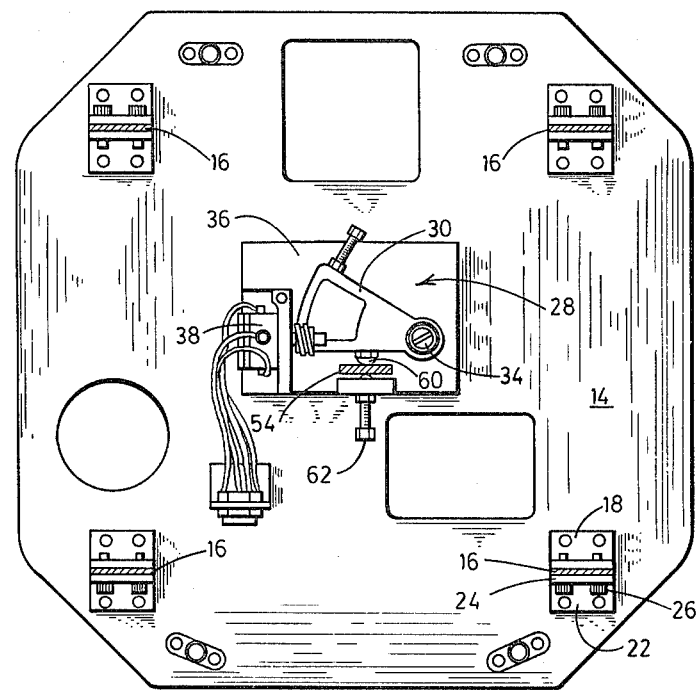
FIG. 4 is a sectioned view taken generally along lines 4—4 of FIG. 2 illustrating an interconnected pivotal arm and potentiometer employed by the skin friction measuring device as shown in FIGS. 1 and 2.

As can be seen, FIG. 4, each of the brackets 18 and 20 includes a flat base 22 and a receiver 24 normally related to the base 22, preferably integrally related therewith. Each of the receivers 24 is configured to form a slot dimensioned to receive an end portion of a flexural member 16 which is, in turn, affixed thereto through the use of fasteners 26 of any suitable design, including rivets, screws, and the like.

It is important to note that the flexural members 16 are commonly oriented so as to accommodate linear displacement of the friction plate 12, relative to a base plate 14, preferably in paralleling planes. Thus displacement of the friction plate 12, relative to the base plate 14, is facilitated as an airstream is caused to flow across the external surface of the friction plate and frictional resistance is offered thereto.

Deflection of the friction plate 12 is detected by motion measuring means, generally designated 28. The motion measuring means includes an arm 30 pivotally mounted on a pedestal 32 employing a suitable bearing pin 34. This pin 34 serves to support the arm 30 for oscillatory motion as it is imparted thereto. The pedestal 32 is supported by a suitable mounting plate 36, FIG. 5, rigidly affixed to the base plate 14, FIG. 2, employing any suitable means. As a practical matter, the arm 30 functions as a motion amplifier.

Disposed in space relation with the pedestal 32, in close proximity with the projected, free end portion of the arm 30, there is a potentiometer 38 of known design. The potentiometer 38, as shown, is supported by a bracket 40 affixed to the plate 36 in close proximity with the arm 30 and includes a rigid support 42 upon which is mounted a rotatable spool 44. The spool is connected to the end portion of the arm 30 through a suitable link, comprising a flexible line 45. As shown, the line is disposed in an arcuate channel, not designated, defined about the end of the arm. The spool 44 is, in turn, connected mechanically to a wiper 46, schematically shown in FIG. 8, mounted within a housing 48 affixed to the bracket 40. It will be appreciated that as angular displacement is imparted to the spool 44, through displacement of the arm 30, the electrical resistance through the circuit of the potentiometer including the wiper 46 is varied. In practice, suitable leads, generally designated 50, and a cannon plug 51 are provided for connecting the potentiometer 38 to a source of electrical potential to be applied across the potentiometer. As a practical matter, a suitable spring, not shown, is connected with the potentiometer, the purpose of which is continuously to urge the arm 30 toward its initial or starting position.

Figure 6:
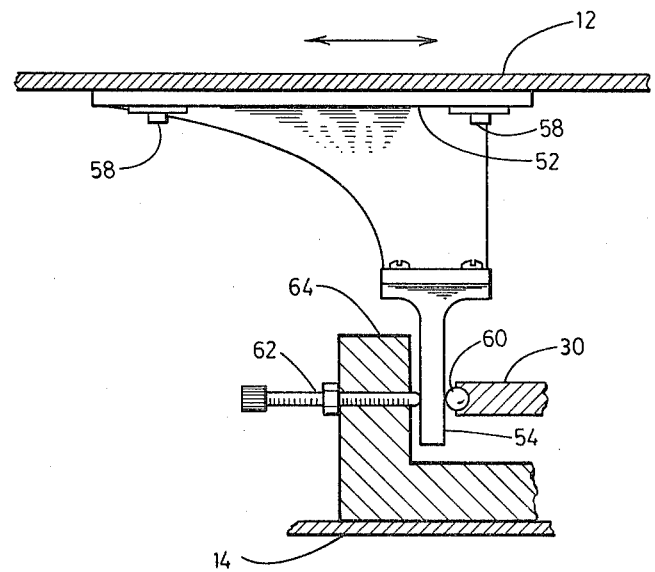
FIG. 6 is a fragmented sectional view depicting a point contact for a spherical bearing mounted on the pivotal arm, whereby forces are transferred to the arm through a point contact with the bearing.

Affixed to the friction plate 12 and projected downwardly therefrom is a mount 52 to which is affixed an actuator spur 54, as best illustrated in FIG. 6. In practice, the mount 52 is seated on and affixed to the underside of the friction plate 12 and projects therefrom to terminate in a bracket 56, FIG. 2, from which depends the actuator spur 54. Suitable fasteners 58, such as screws, rivets, and the like, are employed for securing the mount 52 to the friction plate 12, as well as for coupling the actuator spur 54 to the bracket 56. It should be appreciated that the actuator spur 54 projects from the underside of the friction plate 12 into close proximity with the projected end portion of the arm 30, adjacent a side surface thereof, and in a position to be engaged thereby. As a practical matter, a spherical bearing 60 is mounted on the edge surface of the arm 30 in a position to engage the actuator spur 54, whereby a point contact therebetween is accommodated in order to reduce the effects of motion imparted to the friction plate 12 in directions other than that required in obtaining skin friction measurements. Where desired, an adjustable motion limiting stop 62 is provided for positioning the actuator spur 54 at its initial or null position.

In view of the foregoing, it should now be apparent that the actuator spur 54 projects from the friction plate 12 and engages the spherical bearing 60 for purposes of imparting pivotal motion to the arm 30 as motion is imparted to the plate 12 and that resultant motion is imparted to the wiper 46 of the potentiometer 38 for varying the resistance thereof, whereby the voltage of the output thereof is varied.

OPERATION

It is believed that in view of the foregoing description the operation of the device is apparent, however, in the interest of completeness it will be reviewed.

The device 10 which embodies the principles of the instant invention is provided with a friction plate 12 having an external surface the frictional characteristics of which are to be studied. The device 10 now is mounted at a suitable location, such as within the fuselage for a selected aircraft A. Suitable fasteners which accommodate the coupling of the device 10 with the air frame of the aircraft are employed for this purpose.

As shown, the device 10 is so mounted that the friction plate 12 is positioned to be in contiguity with an airstream as it is caused to flow thereover when the aircraft is in flight. As a practical matter, the base plate 14 is mounted on supporting ribs and the like for the air frame, employing suitable fasteners, not shown. Moreover, while the device 10 is particularly suited for use aboard an aircraft in flight, the device is equally suited for wind-tunnel testing operations, as aforementioned.

Preferably, the device 10 is connected with an electrical circuit through the use of the cannon plug 51.

With the device 10 thus mounted aboard an aircraft the flexural members 16 are positioned to flex in directions paralleling the intended flow of the airstream thereacross. Where so desired the initial position of the spur 54 is established through a manipulation of the motion limiting stops 62, while a spring, aforementioned, but not shown, is provided for assuring that the arm 30 remains in engaged relation with the spur when the arm is in its initial position.

Once the aircraft A is launched, an airstream is established across the surface of the friction plate 12. Due to the drag resulting from the friction established between the surface of the friction plate 12 and the airstream, motion is induced in the friction plate. Such motion is accommodated by deflection of the flexural members 16. As motion is thus induced in the friction plate the spur 54 acts against the spherical bearing 60 causing the arm 30 to pivot about the bearing pin 34. As a consequence of the pivotal motion thus imparted to the arm 30 rotation of the spool 44 for the potentiometer 38 occurs. Angular displacement of the spool caused by the wiper 46 is displaced along the resistor, not designated, of the potentiometer 38. The resulting change in resistance is proportional to the displacement or positional change of the plate 12 as it is induced by the airstream acting thereon. The change in resistance of the potentiometer 38 results in a proportional change in the voltage of the potentiometer's output and is detected employing suitable circuitry, not shown. Thus an output signal is derived from the potentiometer 38 which, in effect, comprises intelligence indicative of the skin friction characteristics for the surface of the plate 12. The plate 12, where so desired, may be provided as one of a plurality of interchangeable plates, with one plate of the plurality serving as a "standard".

In view of the foregoing, it is believed to be readily apparent that the skin friction measuring device of the instant invention comprises a practical solution to the problems heretofore plaguing designers of aircraft components requiring data relating to skin friction resulting from airstreams established thereacross.

What is claimed is:

1. A skin friction measuring device for an aircraft comprising:
    A. a base plate adapted to be mounted on an aircraft;
    B. a friction plate adapted to be disposed in contiguous relation with an airstream as the airstream is caused to flow over the aircraft;
    C. support means mounting said friction plate on said base plate in spaced relation therewith, and supporting said friction plate for skin friction induced displacement; and
    D. displacement measuring means connected to said friction plate for providing an electrical output signal indicative of the magnitude of skin friction induced displacement of said friction plate as the airstream is caused to flow thereover, including an electrical potentiometer adapted to be connected to a source of electrical potential and pivotally displaceable arm connected to the potentiometer for varying the electrical resistance of the potentiometer proportionally to pivotal displacement imparted to the arm, and motion transfer linkage interconnecting said friction plate with said arm for imparting pivotal displacement to said arm proportionally to skin friction induced displacement imparted to said friction plate as the airstream is caused to flow thereover, whereby the electrical resistance to said potentiometer is varied proportionally to the skin friction induced displacement of the friction plate.

2. A skin friction measuring device as defined in claim 1 wherein said mounting means comprises a plurality of flexural membes extended between said base plate and said friction plate adapted to accommodate motion of said friction plate relative to said base plate as the airstream is caused to flow over the surface thereof.

3. A device as defined in claim 1 wherein said arm is pivotally mounted on said base plate and said motion transfer linkage includes:
    A. a rigid spur projected from said friction plate toward said base plate into juxtaposition with said arm; and
    B. a spherical bearing mounted on the arm and disposed in point-contact with the spur.

4. A device as defined in claim 1 wherein said potentiometer includes a rotatable spool and means including a flexible link interconnecting said pivotal arm and said spool.

5. A skin friction measuring device for measuring the resistance of an aerodynamic surface to an airstream passing thereacross, comprising:
    A. a base plate adapted to be mounted in an opening defined in the surface of an aircraft;
    B. a friction plate having an outer surface the curvature of which conforms to the curvature of the external surface of said aircraft adjacent said opening and adapted to be disposed in a flush relationship with the external surface in contiguous relation with an airstream as it is caused to flow over said external surface;
    C. a plurality of flexural members mounting said friction plate on said base plate supporting said friction plate for skin-friction drag induced displacement; and
    D. motion measuring means for measuring displacement of said friction plate including a rigid spur mounted on the friction plate and projected toward said base plate, an arm supported by said base plate for pivotal motion in a plane paralleling the plane of said friction plate disposed in contiguity with said spur and characterized by a spherical bearing mounted on the arm and disposed in point-contact with said spur, a potentiometer adapted to be connected to a source of electrical potential including an angularly displaceable spool for varying the electrical resistance of the potentiometer, and a flexible link interconnecting said arm with said spool, whereby airstream-induced displacement of said friction plate is transferred through said arm to the spool of said potentiometer for varying the electrical resistance of said potentiometer proportionally to the magnitude of airstream-induced displacement of said friction plate.

* * * * *